(12) United States Patent
Wang et al.

(10) Patent No.: US 7,094,723 B2
(45) Date of Patent: Aug. 22, 2006

(54) CATALYSTS CONTAINING AT LEAST ONE HETEROCYCLIC LIGAND FOR IMPROVING THE CATALYSTS' PERFORMANCE OF OLEFIN POLYMERIZATION

(75) Inventors: Shaotian Wang, Mason, OH (US); Clifford C. Lee, Mason, OH (US); Mark P. Mack, Westchester, OH (US)

(73) Assignee: Equistar Chemicals LP, Houston, TX (US)

( * ) Notice: Subject to any disclaimer, the term of this patent is extended or adjusted under 35 U.S.C. 154(b) by 485 days.

(21) Appl. No.: 10/124,991

(22) Filed: Apr. 18, 2002

(65) Prior Publication Data

US 2003/0203807 A1 Oct. 30, 2003

(51) Int. Cl.
   *B01J 31/16* (2006.01)
   *C08F 4/42* (2006.01)
   *C08F 4/64* (2006.01)

(52) U.S. Cl. .......................... 502/103; 556/51; 556/13; 556/14; 526/172; 526/161; 526/134

(58) Field of Classification Search ................. 556/51, 556/52; 526/161, 172; 502/103, 200, 208
See application file for complete search history.

(56) References Cited

U.S. PATENT DOCUMENTS

| | | | |
|---|---|---|---|
| 4,157,435 A * | 6/1979 | Toyota et al. ............ | 526/125.3 |
| 4,202,050 A * | 5/1980 | Klein ........................ | 367/105 |
| 5,064,802 A | 11/1991 | Stevens et al. | |
| 5,066,741 A * | 11/1991 | Campbell, Jr. .............. | 526/171 |
| 5,438,090 A * | 8/1995 | Matsubara et al. ......... | 524/490 |
| 5,539,124 A | 7/1996 | Etherton et al. | |
| 5,554,775 A | 9/1996 | Krishnamurti | |
| 5,599,761 A | 2/1997 | Turner | |
| 5,627,244 A * | 5/1997 | Sato ........................... | 526/92 |
| 5,637,659 A | 6/1997 | Krishnamurti | |
| 5,637,660 A | 6/1997 | Nagy et al. | |
| 5,721,327 A * | 2/1998 | Santi et al. ................. | 526/133 |
| 5,756,611 A | 5/1998 | Etherton et al. | |
| 5,880,241 A | 3/1999 | Brookhart et al. | |
| 5,902,866 A | 5/1999 | Nagy et al. | |
| 6,350,831 B1 * | 2/2002 | Takemori et al. .......... | 526/160 |
| 2004/0082727 A1 * | 4/2004 | Lin et al. .................. | 525/331.9 |

OTHER PUBLICATIONS

Repo et al. J. Organomet. Chem. 1997, 541, 363-366.*
Klein et al. Eur. J. Inorg. Chem. 1998, 621-627.*
Darensbourg et al. Inorg. Chem. 2000, 39, 1578-1585.*
D.S. Matteson and J.W. Wilson, *Organometallics* 1985, 4, 1690-1692, An α-Lithio Boronic Ester from an α-Trimethylstar Boronic Ester.

Carbanions from Deprotonation of α-(Phenylthio)alkaneboronic Esters, American Chemical Society, 1978, p. 1325.
D.S. Matteson and Karl H. Arne, Organometallics 1982, 1, 280-288, Carbanions from α-Phenylthio Boronic Esters as Synthetic Intermediates, American Chemical Society.
D.S. Matteson and D. Majumdar, Organometallics, 1983, 2, 230-236, α-Trimethylsilyl Boronic Esters. Pinacol Lithio(trimethylsilyl)methaneboronate, Homologation of Boronic Comparisons with Some Phosphorus and Sulfur Analogues.
G. Neumann and W.P. Neumann, Journal of Organometallic Chemistry, 1972, p. 293-306.
G. Zweifel and N.R. Pearson, Thexylchloroborne. A Versatile Reagent for the Preparation of Mixed Thexyldiorganoboranes, J. Am. Chem. Soc. 1980, 102, 5919-5920.
"Simply Substitute Boraethenes", Agnew, Chem. Int. Ed. Engl. 24 (1985) No. 12, pp. 1065-1066.
"Regiochemical control in the Hydrostannylation of Aryl Substitute Alkynes: a Stereoselective Synthesis of Disubstituted Vinylstannanes", Synlett 1999, pp. 246-248.
"An Improved Synthesis of 1,4-Diynes", 1979 Georg Thieme Publishers, pp. 292-293.
"A New Approach for the Generation and Reaction of Organotin Hydrides: The Development of Reactions Catalytic in Tin", J. Org. Chem. 1999, 64, pp. 342-343.
"Unique Property of Copper(i) Chloride as a Radical Initiator as well as a Lewis Acid: Application to CuCl-Catalyzed Aldol Reaction of α,β-Unsaturated Ketones with Bu$_3$, SnH", Tetrahedron Letters 40 (1999) pp. 2133-2136.
"3-Phenyl-3-Benzoborepin, A Carbon-Boron Heterocycle with Aromatic Character", Tetrahearon Letters No. 14, pp. 1263-1266, 1967.
"Application of Fluoride-Catalyzed Silane Reductions of Tin Halides to the in Situ Preparation of Vinylstannanes," J. Org. Chem. (1999), 64, pp. 5958-5965.
"The Synthesis and Some Reactions of a Series of "Skipped" Polyacetylenes Containing Terminal Acetylene Groups*", Tetrahedron, vol. 25, pp. 2823-2835.
"The 1-Phenylborabenzene Anion", Journal of American Chemical Society, 1971, pp. 1804-1805.
"Bis (1-substituted-borabenzene) iron Complexes", Journal of American Chemical Society, 1975 (2 pgs.).

* cited by examiner

*Primary Examiner*—David W. Wu
*Assistant Examiner*—Rip A. Lee
(74) *Attorney, Agent, or Firm*—Brooks Kushman, P.C.

(57) ABSTRACT

The present invention provides a non-metallocene catalyst comprising a complex having one or more ligands coordinated a transition metal. The catalyst contains substituents bonded to the transition metal through a heteroatom such as oxygen or sulfur. Furthermore, the complex includes a Group 3 to 10 transition or lanthanide metal and one or more anionic or neutral ligands in an amount that satisfies the valency of the metal such that the complex has a net zero charge. The present invention also discloses a method for preparing the catalyst and polymerizing olefins utilizing the catalyst of the present invention.

35 Claims, No Drawings

CATALYSTS CONTAINING AT LEAST ONE HETEROCYCLIC LIGAND FOR IMPROVING THE CATALYSTS' PERFORMANCE OF OLEFIN POLYMERIZATION

BACKGROUND OF THE INVENTION

1. Field of the Invention

This invention relates to transition metal catalysts having at least one heterocyclic ligand, and in particular, to transition metal catalysts useful for olefin coupling and polymerization.

2. Background Art

The chemical industry uses a wide variety of transition metal complexes as catalysts for organic reactions. Olefin polymerization is an important example of such a reaction. While conventional Ziegler-Natta catalysts continue to dominate the industry, highly active metallocene and non-metallocene single-site catalysts that give new polymers with narrow molecular weight distributions, low densities, and good comonomer incorporation are emerging.

Transition metal complexes used to polymerize olefins are normally non-zero-valent metals (e.g., $Ti^{4+}$, $ZR^{4+}$, $Sc^{3+}$) surrounded by anionic ligands (e.g., chloride, alkyl, cyclopentadienyl) that satisfy the valency of the metal and often improve the solubility of the catalyst in the reaction medium. Anionic ligands can dramatically affect catalyst activity and polymer properties. Thus, a catalyst structure can be fine-tuned to give polymers with desirable properties. Furthermore, the anionic ligand will affect the stability of the transition metal complexes.

Metallocene polymerization catalysts contain one or two cyclopentadienyl groups as anionic ligands. These serve to stabilize the active catalytic species, modulate the electronic and steric environment around the active metal center, and maintain the single-sited nature of the catalyst. Polymers with narrow molecular weight and composition distributions are formed from these metallocene catalysts. Such complexes frequently contain cyclopentadienyl groups. Putting substituents on the cyclopentadienyl ring, for example, changes the geometry and electronic character of the active site.

Another class of anionic ligands is those which are heteroatomic ring ligands which are isolobal to the cyclopentadienyl ring; that is, the orbital interaction of the metal with the ligand is similar in both cases. Examples of such ligands are boraaryl (see, e.g., U.S. Pat. No. 5,554,775), pyrroyl and indolyl anions (U.S. Pat. No. 5,539,124), azaborolinyl groups (U.S. Pat. No. 5,902,866), indole-indenyl groups, phospholyl anions, and tris(pyrazolyl)borate anions.

Frequently, transition metal catalyst exhibit sensitivity to moisture and oxygen and poor stability during storage. This poor sensitivity and stability is often caused by a halogen attached to the transition metal or by an alkyl or aryl ligand that is attached to the transition metal of the catalyst by a bond to a carbon atom.

SUMMARY OF THE INVENTION

It is an object of the present invention to provide an improved olefin polymerization catalyst.

It is another object of the present invention to provide an improved olefin polymerization catalyst that includes an alkyl or aryl ligand that is not bonded to the transition metal directly with carbon.

It is another object of the present invention to provide an improved olefin polymerization catalyst that includes heterocyclic ligand.

In one embodiment of the present invention, a transition metal catalyst having Formula I is provided.

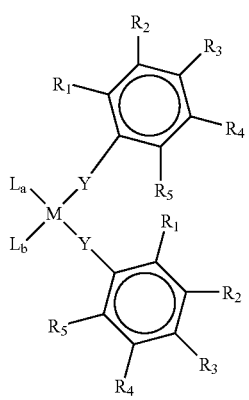

wherein
M is a metal selected from Groups 3 to 10 and the lanthanide series of the Periodic Table;

$R_1$, $R_2$, $R_3$, $R_4$, and $R_5$ are independently hydrogen, $C_{1-10}$ alkyl, $C_{6-10}$ aryl, $C_{7-15}$ aralkyl, $C_{1-10}$ alkoxy, or $C_{1-10}$ alkylamino or C2-20 dialkylamino each of these groups optionally substituted with halogen, cyano, $C_{1-4}$ alkoxy, or $C_{1-4}$ alkyl;

Y is a heteroatom capable of bonding; and

La and Lb are each independently an anionic or neutral ligand wherein La and Lb are optionally bridged together with an alkylene or heteroalkylene.

In another embodiment of the present invention, a catalyst having Formula II is provided:

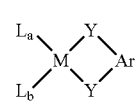

wherein La, Lb, M, and Y are the same as described above for Formula I; and Ar is substituted or unsubsituted hydrocarbon having a least one phenyl.

In another embodiment of the present invention, a method of preparing the catalyst described by Formula I is provided. The method comprises reacting a dihalide with Formula A:

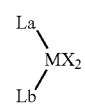

with substituted phenyl B:

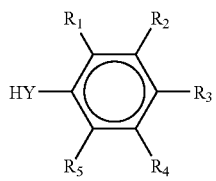

to form compounds described by Formula I, wherein X is a halogen; and $R_1$, $R_2$, $R_3$, $R_4$, $R_5$, M, La, Lb, and Y are the same as defined above.

In another embodiment of the present invention, a method of preparing the catalyst described by Formula II is provided. The method comprises reacting a dihalide with Formula A:

with B':

to form compounds described by Formula II, wherein X is a halogen; and $R_1$, $R_2$, $R_3$, $R_4$, $R_5$, M, La, Lb, Ar, and Y are the same as defined above.

In another embodiment of the present invention, a method of preparing the catalyst described by Formula I is provided. The method comprises reacting a compound having Formula C:

with substituted phenyl B:

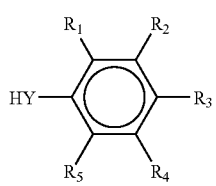

to form compounds described by Formula I, where $R_7$ is a $C_{1-10}$ alkyl; and $R_1$, $R_2$, $R_3$, $R_4$, $R_5$, M, La, Lb, and Y are the same as defined above.

In yet another embodiment of the present invention, a method of preparing the catalyst described by Formula I is provided. The method comprises reacting a dihalide with Formula A:

with salt D:

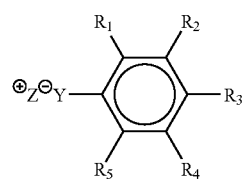

to form compounds described by Formula I, wherein X is a halogen; Z is Li, Na, or K; and $R_1$, $R_2$, $R_3$, $R_4$, $R_5$, M, La, Lb, and Y are the same as defined above.

In still another embodiment of the present invention, a process for coupling two or more olefins is provided. Such a process includes dimerization and polymerization. In the processes of the present invention, the complexes described by Formula I and II are used to couple olefins.

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

The term "ligand" as used herein refers to functional coordinating groups which have one or more pairs of electrons available for the formation of coordinate bonds.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, halogen, nitro, cyano, oxo, thio, —OH, —SH, —F, —CF$_3$, —OCF$_3$, —NO$_2$, —CO$_2$H, —CO$_2$C$_1$–C$_6$ alkyl, —NH$_2$, —NHC$_1$–C$_6$ alkyl, —OCH$_2$O—, —CONR$^8$R$^9$, or —N(C$_1$–C$_6$alkyl)$_2$. Preferably, alkyl is a "lower alkyl" as defined below.

The term "lower alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Sometimes herein lower alkyl is referred to as "C$_1$–C$_6$alkyl."

The terms "alkoxy" as used herein refers to O-alkyl where alkyl is defined above.

The term "alkylamino" denotes amino groups which have been substituted with one alkyl radical. Preferred alkylamino have alkyl portions having 1 to 6 carbon atoms.

The term "dialkylamino" denotes amino groups which have been substituted with two alkyl radicals. Preferred dialkylamino have alkyl portions having 1 to 6 carbon atoms.

The term "aryl" as used herein refers to an aromatic ring which is unsubstituted or optionally substituted by 1 to 4 substituents selected from lower alkyl, lower alkoxy, lower thioalkoxy, halogen, nitro, cyano —OH, —SH, —F, —$CF_3$, —$OCF_3$, —$NO_2$, —$CO_2H$, —$CO_2C_1$–$C_6$ alkyl, —$NH_2$, —$NHC_1$–$C_6$ alkyl, —$CONR^8R^9$, —$SO_2$alkyl, —$SO_2NH_2$, or —$N(C_1$–$C_6alkyl)_2$. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, thienyl, furanyl, pyrrolyl, pyridyl, pyrimidyl, imidazoyl, pyrazinyl, oxazolyl, thiazolyl, naphthyl, benzothienyl, benzofuranyl, indolyl, quinolinyl, isoquinolinyl, and quinazolinyl, and the like.

The term "aralkyl" as used herein refers to an alkyl radical to which is appended an aryl group. Representative arylalkyl groups include benzyl, phenylethyl, hydroxybenzyl, fluorobenzyl, fluorophenylethyl, and the like. The arylalkyl groups of this invention can be optionally substituted with the same substituents listed above for aryl.

The term "halogen" includes chlorine, fluorine, bromine, and iodine.

The term "heteroatom" as used herein represents oxygen, nitrogen, phosphorus, boron, or sulfur (O, N, P, B, or S). It is understood that alkyl chains interrupted by one or more heteroatoms means that a carbon atom of the chain is replaced with a heteroatom having the appropriate valency. Preferably, an alkyl chain is interrupted by 1 to 4 heteroatoms and that two adjacent carbon atoms are not both replaced. Examples of such groups include methoxymethyl, 3-thiomethylpropyl, and 2-thiomethoxyethoxymethyl The term "heterocycle" means a saturated or unsaturated mono- or polycyclic (i.e. bicyclic) ring incorporating one or more (i.e. 1–4) heteroatoms selected from N, O, P, B, and S. It is understood that a heterocycle is optionally substituted with —OH, —O(alkyl), SH, S(alkyl), amine, halogen, acid, ester, amide, amidine, alkyl ketone, aldehyde, nitrile, fluoroalkyl, nitro, sulphone, sulfoxide or $C_{1-6}$ alkyl.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted. The alkylene group can also be substituted with one or more of the substituents selected from lower alkyl, lower alkoxy, lower thioalkoxy, —$O(CH_2)_{0-2}CF_3$, halogen, nitro, cyano, =O, =S, —OH, —SH, —$CF_3$, —$CO_2H$, —$CO_2C_1$–$C_6$ alkyl, —$NH_2$, —$NHC_1$–$C_6$ alkyl, —CONR'R", or —$N(C_1$–$C_6alkyl)_2$ where R' and R" are independently alkyl, alkenyl, alkynyl, aryl, or joined together to form a 4 to 7 member ring. Preferred alkylene groups have from 1 to 6 carbon atoms ($C_1$–$C_6$ alkyl).

The term "heterocycloalkylene" as used herein, refers to a cycloalkylene group that includes one or more heteroatoms such as oxygen, sulfur, or nitrogen (with valence completed by hydrogen or oxygen) in the carbon ring.

In an embodiment of the present invention, a transition metal catalyst having Formula I is provided:

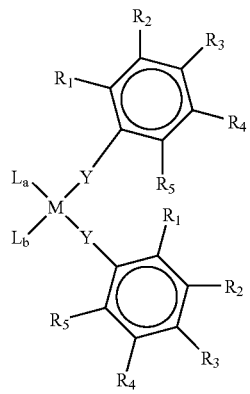

I wherein
  M is a metal selected from Groups 3 to 10 and the lanthanide series of the Periodic Table;
  $R_1$, $R_2$, $R_3$, $R_4$, and $R_5$ are independently hydrogen, $C_{1-10}$ alkyl, $C_{6-10}$ aryl, $C_{7-15}$ aralkyl, $C_{1-10}$ alkoxy, $C_{1-10}$ alkylamino, or $C_{2-20}$ dialkylamino each of these groups optionally substituted with halogen, cyano, $C_{1-4}$ alkoxy, or $C_{1-4}$ alkyl;
  Y is a heteroatom attaching to M;
  La and Lb are each independently an anionic or neutral ligand wherein La and Lb are optionally bridged together with an alkylene or heteroalkylene.

Preferably, La is an anionic or neutral heterocylic ligand and Lb is an anionic or neutral non-heterocyclic ligand; and M is a metal selected from Groups 3 to 10 of the Periodic Table. More preferably, M is a metal selected from Groups 3 to 4 of the Periodic Table; and most preferably, M is titanium, zirconium, and hafnium. Furthermore, Y is preferably oxygen, sulfur, nitrogen, or phosphorus; and more preferably, Y is oxygen or sulfur.

In another embodiment of the present invention, a catalyst having Formula II is provided:

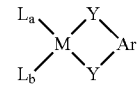

II wherein La, Lb, M, and Y are the same as described above for Formula I; and Ar is substituted or unsubstituted hydrocarbon having a least one phenyl.

The anionic or neutral ligands, include but are not limited to unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, boraaryl groups, or the like, and combinations of these. Examples of neutral ligands are carbonyl, $\eta^6$-aryl, $\eta^4$-butadiene, $\eta^4$-cyclobutadiene, $\eta^4$-cyclooctatetraene, tertiary phosphine, and the like. Other examples of suitable anionic or neutral ligands appear in U.S. Pat. Nos. 5,756,611, 5,637,659, 5,637,660, 5,554,775, and 5,539,124, the teachings of which are incorporated herein by reference.

In another embodiment of the invention, the transition metal complex of the present invention further comprises an activator. Generally, the activator converts the complex to a cationically active species. The catalysts are especially valuable for polymerizing olefins, such as ethylene, propylene, and/or other a-olefins such as 1-butene, 1-hexene, or 1-octene. Suitable activators are well known in the art. Preferred activators include alumoxanes (e.g., methyl alumoxane (MAO), PMAO, ethyl alumoxane, diisobutyl alumoxane), alkylaluminum compounds (triethylaluminum, diethylaluminum chloride, trimethylaluminum, trisisobutylaluminum), and the like. Such activators are generally used in an amount within the range of about 0.01 to about 100,000, preferably from about 1 to about 1,000, moles per mole of transition metal complex. Preferred activators also include acid salts that contain non-nucleophilic anions. These compounds generally consist of bulky ligands attached to boron or aluminum. Examples include lithium tetrakis(pentafluorophenyl) borate, lithium tetrakis(pentafluorophenyl) aluminate, anilinium tetrakis(pentafluorophenyl) borate, triphenylcarbenium tetrakis(pentafluorophenyl) borate, and the like. These activators are generally used in an amount within the range of about 0.01 to about 1000, preferably from about 1 to about 10, moles per mole of transition metal complex. Suitable activators also include trialkyl or triarylboron compounds such as tris(pentafluorophenyl)borane, tris(pentabromophenyl) borane and trialkyl or triarylaluminum compounds such as tris(penetafluorphenyl)aluminum, and the like. Other suitable activators are described, for example, in U.S. Pat. Nos. 5,756,611, 5,064,802, and 5,599,761, the teachings of which are incorporated herein by reference.

The catalysts are optionally used with an inorganic solid or organic polymer support. Suitable supports include silica, alumina, silica-aluminas, magnesia, titania, clays, zeolites, or the like. The supports can be pretreated thermally, chemically, or both to improve catalyst productivity or product properties. The catalysts can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst. The ligand can also be chemically tethered to the support through a suitable linking group.

In still another embodiment of the present invention, a process for coupling two or more olefins is provided. These coupling processes include but are not limited to dimerization, oligomerization, and polymerization. Such coupling can be conducted in different manners, for instance, in slurry, gas phase, and high temperature solution reactors. In the coupling processes of the present invention, the complexes described by structures I and II are used as catalysts. The process of the present invention comprises:
1) mixing in a reaction vessel a solvent, an activator and a catalyst given by formula I or formula II; and
2) introducing an olefin into the reaction vessel, wherein at least two molecules of the olefin are coupled together.

PREPARATION OF COMPOUNDS OF THE INVENTION

The present invention contains compounds that can be synthesized in a number of ways familiar to one skilled in organic synthesis. The compounds outlined herein can be synthesized according to the methods described below, along with methods typically utilized by a synthetic chemist, and combinations or variations of those methods which are generally known to one skilled in the art of synthetic chemistry. The synthetic route of compounds in the present invention is not limited to the methods outlined below. It is assumed one skilled in the art will be able to use the schemes outlined below to synthesize compounds claimed in this invention. Individual compounds may require manipulation of the conditions in order to accommodate various functional groups. A variety of protecting groups generally known to one skilled in the art may be required. Purification, if necessary, can be accomplished on a silica gel column eluted with the appropriate organic solvent system. Also, reverse phase HPLC may be employed if a compound does not move on silica gel.

The compounds described by Formula I can be made by different routes, for instance, the processes described by Scheme I, Scheme II, and Scheme III. With reference to Scheme I, complex A is reacted with compound B in the presence of amine, $(R_7)_3N$, where $R_7$ is alkyl or aryl to form the compounds described by Formula I.

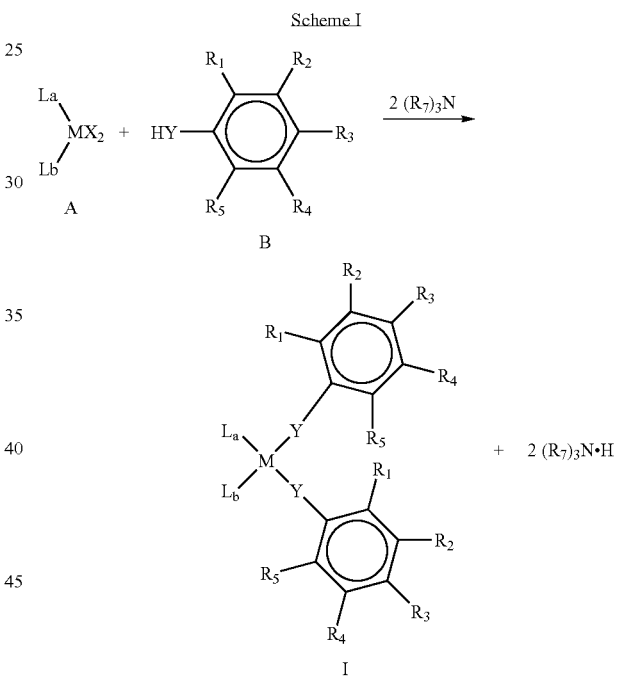

The compounds described by Formula II are preferably made by the process described by Scheme II. With reference to Scheme II complex A is react with compound B' is the presence of the amine, $(R_7)_3N$ to form the compounds described by Formula II, wherein $R_7$ is alkyl or aryl

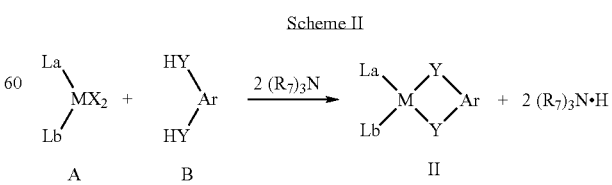

Alternatively, the compounds described by Formula I are made by the process described by Scheme III. With reference to Scheme III compound A is react with the base, $R_7Z$, where Z is Li, Na, or K and $R_7$ is alkyl or aryl, to form compound C. Compound C is then reacted to complex A to form the compounds described by Formula I.

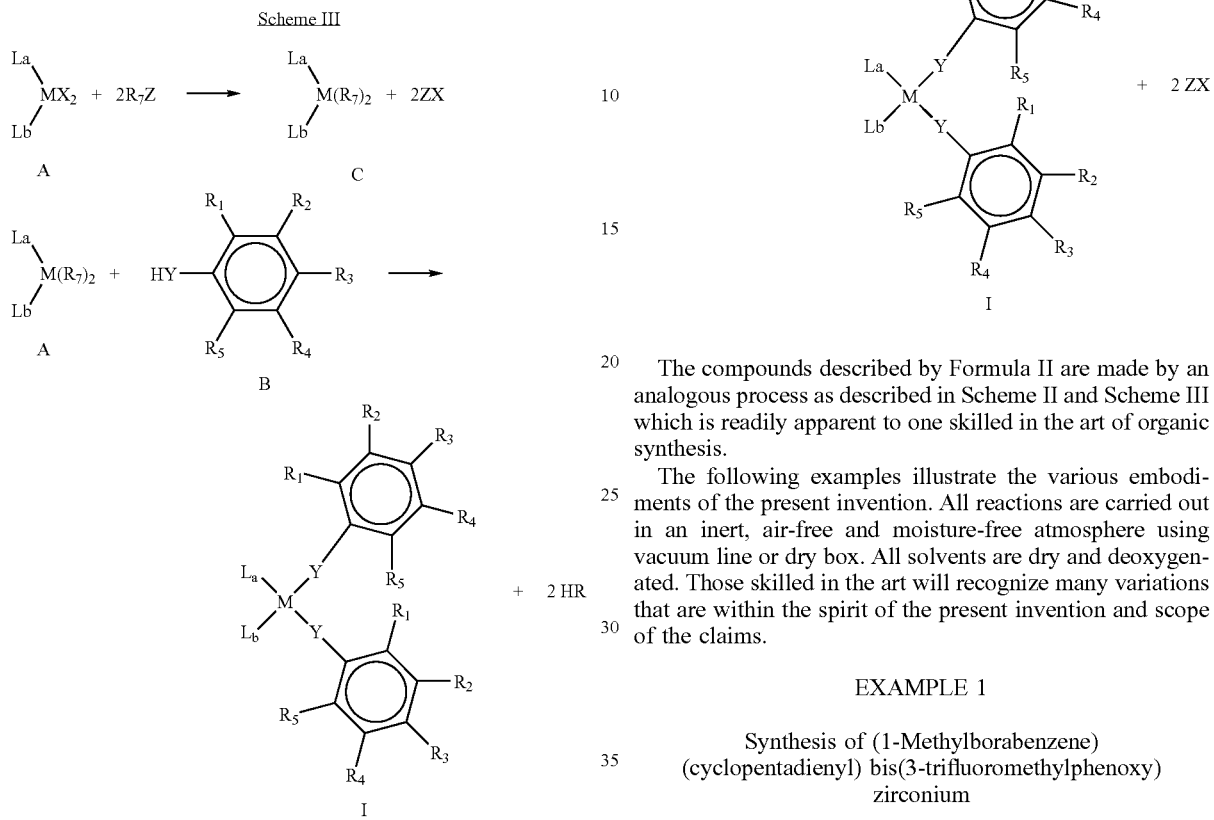

In yet another variation, the compounds described by Formula I are alternatively made by the process described by Scheme IV. With reference to Scheme IV compound B is react with the base, $R_7Z$, to form salt D, wherein Z is Li, Na, or K and $R_7$ is alkyl or aryl, Salt D is then reacted to complex A to form the compounds described by Formula I.

The compounds described by Formula II are made by an analogous process as described in Scheme II and Scheme III which is readily apparent to one skilled in the art of organic synthesis.

The following examples illustrate the various embodiments of the present invention. All reactions are carried out in an inert, air-free and moisture-free atmosphere using vacuum line or dry box. All solvents are dry and deoxygenated. Those skilled in the art will recognize many variations that are within the spirit of the present invention and scope of the claims.

EXAMPLE 1

Synthesis of (1-Methylborabenzene) (cyclopentadienyl) bis(3-trifluoromethylphenoxy) zirconium To a 100 ml Schlenk flask containing 318.2 mg (1 mmole) of (1-methylboratabenzene) (cyclopentadienyl) zirconium dichloride [complex example (a)] in 30 ml diethyl ether and at −78° C., 0.7 ml of 3.0 M methylmagnesium bromide diethyl ether solution (2.1 mmoles) is added slowly under stirring. After warming up to room temperature and stirring other two hours at room temperature, the reaction mixture is filtrated and then the solvent of the filtrate is moved by vacuum. The intermediate product (1-methylboratabenzene) (cyclopentadienyl) dimethyl zirconium can be obtained through re-crystallization from the residue of the filtrate.

To a 50 ml Schlenk flask containing 138.7 mg (0.5 mmole) of (1-methylboratabenzene) (cyclopentadienyl) dimethyl zirconium [intermediate product of $1^{st}$ Step] in 15 ml toluene and at 0° C., 162.1 mg (1 mmole) of Trifluoro-m-Cresol in 10 ml toluene is added slowly under stirring. After warming up to room temperature and stirring one hour at room temperature, toluene of the reaction mixture is moved by vacuum. The desired product (1-methylboratabenzene) (cyclopentadienyl) bis(3-trifluoromethylphenoxy) zirconium can be obtained from the residue of vacuum distillation.

EXAMPLE 2

Synthesis of (1-Methyl-methyl Indoleindenyl) (cyclopentadienyl) bis(2-trifluoromethylphenoxy) zirconium

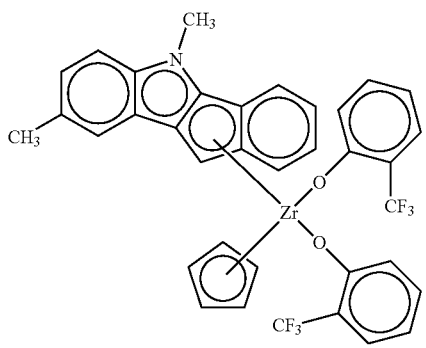

To a 100 ml Schlenk flask containing 1.62 g (10 mmoles) of teifluoro-o-cresol [$HOC_6H_4CF_3$] in 30 ml hexane and at −78° C., 4.2 ml of 2.5 M ⁿButyl lithium hexane solution (10.5 mmoles) is added slowly under stirring. After warming up to room temperature and stirring other two hours at room temperature, the reaction mixture is filtrated and then the solid on the filter is washed by hexane and then dried by vacuum for the intermediate product $LiOC_6H_4CF_3$.

To a 100 ml Schlenk flask containing 459.6 mg (1 mmole) of $(CH_3NC_{16}H_{11})(C_5H_5)ZrCl_2$ [complex example (b)] in 30 ml toluene and at 0° C., 369.6 mg (2.2 mmoles) of $LiOC_6H_4CF_3$ [from 1$^{st}$ step] in 20 ml diethyl ether is added slowly under stirring. After warming up to room temperature and stirring other two hours at room temperature, reaction mixture is filtrated. The toluene and ether of the filtrate are removed by vacuum. The desired product (1-Methyl-methyl Indole-indenyl) (cyclopentadienyl) bis(2-trifluoromethylphenoxy) zirconium can be obtained from the residue of vacuum dry.

EXAMPLE 3

Preparation of a Supported Catalyst

To 2.8 ml of 4.3 M solution of polymethylalumioxane in toluene 0.005 (0.06 mmole) g of the complex formed in Example 1 is added and stirred for 1 hr at ambient temperature. The resulting solution is added slowly to stirred bed of 2.0 g dehydrated silica support to result in a free-flowing catalyst powder, with aluminum to zirconium mole ratio of about 200.

Polymerization of Ethylene

About 0.048 g of the supported catalyst formed above is added to a 1000 ml reactor charged with 500 ml of isobutane and 1 ml of 1M solution of triisobutylaluminum in heptane and ethylene is polymerized at 350 psi ethylene pressure at 70° C. to produce high molecular weight polyethylene.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:
1. A catalyst comprising a complex having Formula I:

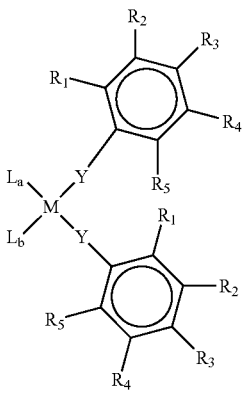

wherein
M is a metal selected from Groups 3 to 10 and the lanthanide series of the Periodic Table;
$R^1$, $R^2$, $R^3$, $R^4$, and $R^5$ are independently hydrogen, $C_{1-10}$ alkyl, $C_{6-10}$ aryl, $C_{7-15}$ aralkyl, $C_{1-10}$ alkoxy, or $C_{1-10}$ alkylamino, or $C_{2-20}$ dialkylamino each of these groups optionally substituted with halogen, cyano, $C_{1-4}$ alkoxy, or $C_{1-4}$ alkyl;
Y is sulfur, nitrogen, or phosphorus; and
La and Lb are each independently an anionic or neutral ligand wherein La and Lb are optionally bridged together with an alkylene or heteroalkylene.

2. The catalyst of claim 1 wherein M is selected from the group consisting of Groups 3 to 4 of the Periodic Table.

3. The catalyst of claim 1 wherein M is selected from the group consisting of titanium, zirconium, and hafnium.

4. The catalyst of claim 1 wherein La and Lb are each independently an anionic ligand selected from the group consisting of unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, and boraaryl.

5. The catalyst of claim 1 wherein La and Lb are each independently a neutral ligand selected from the group consisting of carbonyl, $\eta^6$-aryl, $\eta^4$-butadiene, $\eta^4$-cyclobutadiene, $\eta^4$-cyclooctatetraene, tertiary phosphine, and mixture thereof.

6. The catalyst of claim 1 wherein La is an anionic or neutral heterocyclic ligand and Lb is an anionic or neutral non-heterocyclic ligand.

7. The catalyst of claim 1 further comprising an activator.

8. The catalyst of claim 7 wherein the activator is selected from the group consisting of alumoxanes, alkylaluminum compounds, and mixtures thereof.

9. The catalyst of claim 7 wherein the activator is an acid salt that contain non-nucleophilic anions.

10. The catalyst of claim 7 wherein the activator is selected from the group consisting of tris(pentafluorophenyl)boron, tris(pentabromophenyl) boron, tris(pentafluorophenyl) aluminum, lithium tetrakis(pentafluorophenyl) borate, lithium tetrakis(pentafluorophenyl) aluminate, anilinium tetrakis(pentafluorophenyl) borate, triphenylcarbenium tetrakis(pentafluorophenyl) borate, and mixture thereof.

11. A catalyst comprising a complex having Formula I:

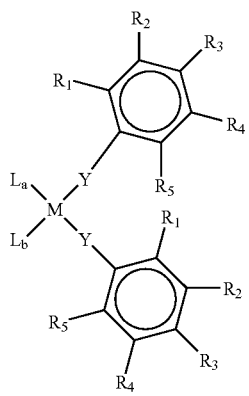

wherein
- M is a metal selected from Groups 3 to 10 and the lanthanide series of the Periodic Table;
- $R^1$, $R^2$, $R^3$, $R^4$, and $R^5$ are independently hydrogen, $C_{1-10}$ alkyl, $C_{6-10}$ aryl, $C_{7-15}$ aralkyl, $C_{1-10}$ alkoxy, $C_{1-10}$ alkylamino, or $C_{2-20}$ dialkylamino each of these groups optionally substituted with halogen, cyano, $C_{1-4}$ alkoxy, or $C_{1-4}$ alkyl;
- Y is sulfur or nitrogen; and
- La and Lb are each independently an anionic or neutral ligand wherein La and Lb are optionally bridged together with an alkylene or heteroalkylene.

12. The catalyst of claim 11, wherein M is selected from the group consisting of Groups 3 to 4 of the Periodic Table.

13. The catalyst of claim 11, wherein M is selected from the group consisting of titanium, zirconium, and hafnium.

14. The catalyst of claim 11 wherein La and Lb are each independently an anionic ligand selected from the group consisting of unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, and boraaryl.

15. The catalyst of claim 11 wherein La and Lb are each independently a neutral ligand selected from the group consisting of carbonyl, $\eta^6$-aryl, $\eta^4$-butadiene, $\eta^4$-cyclobutadiene, $\eta^4$-cyclooctatetraene, tertiary phosphine, and mixture thereof.

16. The catalyst of claim 11, wherein La is an anionic or neutral heterocyclic ligand and Lb is an anionic or neutral non-heterocyclic ligand.

17. The catalyst of claim 11, further comprising an activator.

18. The catalyst of claim 17, wherein the activator is selected from the group consisting of alumoxanes, alkylaluminum compounds, and mixtures thereof.

19. The catalyst of claim 17 wherein the activator is an acid salt that contain non-nucleophilic anions.

20. The catalyst of claim 17 wherein the activator is selected from the group consisting of tris(pentafluorophenyl)boron, tris(pentabromophenyl) boron, tris(pentafluorophenyl) aluminum, lithium tetrakis(pentafluorophenyl) borate, lithium tetrakis(pentafluorophenyl) aluminate, anilinium tetrakis(pentafluorophenyl) borate, triphenylcarbenium tetrakis(pentafluorophenyl) borate, and mixture thereof.

21. A catalyst comprising a complex having Formula I:

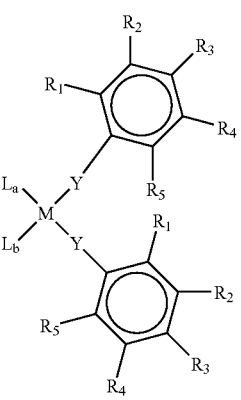

wherein
- M is a metal selected from Groups 3 to 10 and the lanthanide series of the Periodic Table;
- $R^1$, $R^2$, $R^3$, $R^4$, and $R^5$ are independently hydrogen, $C_{1-10}$ alkyl, $C_{6-10}$ aryl, $C_{7-15}$ aralkyl, $C_{1-10}$ alkoxy, $C_{1-10}$ alkylamino, or $C_{2-20}$ dialkylamino each of these groups optionally substituted with halogen, cyano, $C_{1-4}$ alkoxy, or $C_{1-4}$ alkyl;
- Y is a heteroatom; and
- La is a anionic or neutral heterocyclic ligand and Lb is an anionic or neutral non-heterocyclic ligand.

22. The catalyst of claim 21, wherein M is selected from the group consisting of Groups 3 to 4 of the Periodic Table.

23. The catalyst of claim 21, wherein M is selected from the group consisting of titanium, zirconium, and hafnium.

24. The catalyst of claim 21, wherein Y is oxygen, sulfur, nitrogen, or phosphorus.

25. The catalyst of claim 21, further comprising an activator.

26. The catalyst of claim 25, wherein the activator is selected from the group consisting of alumoxanes, alkylaluminum compounds, and mixtures thereof.

27. The catalyst of claim 25 wherein the activator is an acid salt that contain non-nucleophilic anions.

28. The catalyst of claim 25 wherein the activator is selected from the group consisting of tris(pentafluorophenyl)boron, tris(pentabromophenyl) boron, tris(pentafluorophenyl) aluminum, lithium tetrakis(pentafluorophenyl) borate, lithium tetrakis(pentafluorophenyl) aluminate, anilinium tetrakis(pentafluorophenyl) borate, triphenylcarbenium tetrakis(pentafluorophenyl) borate, and mixture thereof.

29. A catalyst comprising a complex having Formula I:

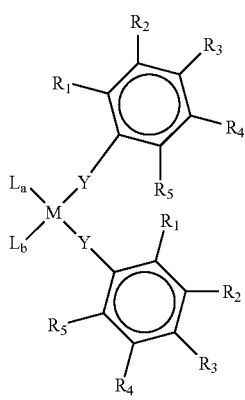

wherein
M is selected from the group consisting of Groups 3 to 4 of the Periodic Table;

$R^1$, $R^2$, $R^3$, $R^4$, and $R^5$ are independently hydrogen, $C_{1-10}$ alkyl, $C_{6-10}$ aryl, $C_{7-15}$ aralkyl, $C_{1-10}$ alkoxy, $C_{1-10}$ alkylamino, or $C_{2-20}$ dialkylamino each of these groups optionally substituted with halogen, cyano, $C_{1-4}$ alkoxy, or $C_{1-4}$ alkyl;

Y is a heteroatom; and

La and Lb are each independently a neutral ligand selected from the group consisting of carbonyl, $\eta^6$-aryl, $\eta^4$-butadiene, $\eta^4$-cyclobutadiene, $\eta^4$-cyclooctatetraene, tertiary phosphine, and mixture thereof.

30. The catalyst of claim 29, wherein M is selected from the group consisting of titanium, zirconium, and hafnium.

31. The catalyst of claim 29, wherein Y is oxygen, sulfur, nitrogen, or phosphorus.

32. The catalyst of claim 29, further comprising an activator.

33. The catalyst of claim 32, wherein the activator is selected from the group consisting of alumoxanes, alkylaluminum compounds, and mixtures thereof.

34. The catalyst of claim 32 wherein the activator is an acid salt that contains non-nucleophilic anions.

35. The catalyst of claim 32 wherein the activator is selected from the group consisting of tris(pentafluorophenyl)boron, tris(pentabromophenyl) boron, tris(pentafluorophenyl) aluminum, lithium tetrakis(pentafluorophenyl) borate, lithium tetrakis(pentafluorophenyl) aluminate, anilinium tetrakis(pentafluorophenyl) borate, triphenylcarbenium tetrakis(pentafluorophenyl) borate, and mixture thereof.

* * * * *